(12) United States Patent
Stamler et al.

(10) Patent No.: US 8,871,506 B2
(45) Date of Patent: *Oct. 28, 2014

(54) METHODS FOR TREATING CARDIO PULMONARY DISEASES WITH NO GROUP COMPOUNDS

(71) Applicant: Duke University, Durham, NC (US)

(72) Inventors: Jonathan S. Stamler, Chapel Hill, NC (US); Eric J. Toone, Durham, NC (US); Andrew J. Gow, Princeton, NJ (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,202

(22) Filed: Mar. 21, 2013

(65) Prior Publication Data

US 2013/0210136 A1 Aug. 15, 2013

Related U.S. Application Data

(60) Division of application No. 11/231,162, filed on Sep. 20, 2005, now abandoned, which is a division of application No. 10/069,114, filed as application No. PCT/US00/20784 on Aug. 18, 2000, now Pat. No. 6,945,247, which is a continuation-in-part of application No. 09/390,215, filed on Sep. 8, 1999, now Pat. No. 6,314,956.

(51) Int. Cl.
| | |
|---|---|
| *A61M 15/00* | (2006.01) |
| *C12Q 1/68* | (2006.01) |
| *C12N 5/078* | (2010.01) |
| *A61K 33/00* | (2006.01) |
| *A61K 31/197* | (2006.01) |
| *A61K 33/04* | (2006.01) |
| *A61K 31/21* | (2006.01) |

(52) U.S. Cl.
CPC ............... *C12N 5/0641* (2013.01); *A61K 33/00* (2013.01); *A61M 2202/0275* (2013.01); *A61K 31/197* (2013.01); *A61K 33/04* (2013.01); *A61K 31/21* (2013.01)
USPC ... 435/325; 128/200.14; 514/509; 424/93.73; 435/6

(58) Field of Classification Search
USPC ................ 435/325, 6; 128/200.14; 424/93.73
See application file for complete search history.

(56) References Cited

U.S. PATENT DOCUMENTS

| | | |
|---|---|---|
| 4,353,843 A | 10/1982 | Doumaux, Jr. et al. |
| 4,721,060 A | 1/1988 | Cannon et al. |

(Continued)

FOREIGN PATENT DOCUMENTS

| | | |
|---|---|---|
| EP | 0006611 A1 | 1/1980 |
| EP | 0655432 A1 | 5/1995 |

(Continued)

OTHER PUBLICATIONS

CAPLUS Chemical Abstract Accession No. 115:56107. (1991).

(Continued)

*Primary Examiner* — Ernst V Arnold
*Assistant Examiner* — Hong Yu
(74) *Attorney, Agent, or Firm* — Cooley LLP; Ivor Elrifi; Matthew Pavao

(57) ABSTRACT

The present invention relates to methods of treatment of pulmonary disorders associated with hypoxemia and/or smooth muscle constriction and/or inflammation; treatment of cardiac and blood disorders; treatment of patient in need of improved oxygenation, blood flow of and/or thinning of blood and method of screening drugs that increase level of nitrosoglutathione in airway lining fluid.

2 Claims, 10 Drawing Sheets

(56) References Cited

U.S. PATENT DOCUMENTS

| | | | |
|---|---|---|---|
| 4,908,466 | A | 3/1990 | Nelson |
| 5,278,192 | A | 1/1994 | Fung et al. |
| 5,412,147 | A | 5/1995 | Landscheidt et al. |
| 5,485,827 | A | 1/1996 | Zapol et al. |
| 5,489,610 | A | 2/1996 | Fung et al. |
| 5,570,683 | A | 11/1996 | Zapol |
| 5,571,524 | A | 11/1996 | Kitakaze et al. |
| 5,583,101 | A | 12/1996 | Stamler et al. |
| 5,649,322 | A | 7/1997 | Landscheidt et al. |
| 5,713,349 | A | 2/1998 | Keaney |
| 5,770,645 | A | 6/1998 | Stamler et al. |
| 5,823,180 | A | 10/1998 | Zapol |
| 5,824,669 | A | 10/1998 | Garvey et al. |
| 5,863,890 | A | 1/1999 | Stamler et al. |
| 5,873,359 | A | 2/1999 | Zapol et al. |
| 5,958,427 | A | 9/1999 | Salzman et al. |
| 5,962,421 | A | 10/1999 | Esteras et al. |
| 6,153,186 | A | 11/2000 | Stamler et al. |
| 6,203,789 | B1 | 3/2001 | Stamler et al. |
| 6,314,956 | B1 | 11/2001 | Stamler et al. |
| 6,916,471 | B2 | 7/2005 | Stamler et al. |
| 6,945,247 | B1* | 9/2005 | Stamler et al. ........... 128/200.14 |
| 7,045,152 | B2 | 5/2006 | Stamler |
| 7,329,543 | B2 | 2/2008 | Stamler et al. |
| 2007/0191478 | A1* | 8/2007 | Stamler et al. ................ 514/509 |

FOREIGN PATENT DOCUMENTS

| | | | | |
|---|---|---|---|---|
| WO | WO-9210228 | A1 | | 6/1992 |
| WO | WO-9401103 | A1 | | 1/1994 |
| WO | WO 98/34955 | | * 8/1998 | ........... C07K 14/805 |
| WO | WO-0067754 | A1 | | 11/2000 |
| WO | WO-0117596 | A1 | | 3/2001 |
| WO | WO-0232418 | A1 | | 4/2002 |

OTHER PUBLICATIONS

Cederqvist et al. "Direct Demonstration of NO Formation in Vivo from Organic Nitrites and Nitrates, and Correlation to Effects on Blood Pressue and to in Vitro Effects." *Biochem. Pharmacol.* 47.6(1994):1047-1053.

Dwenger et al. "Ascorbic Acid Reduces the Endotoxin-Induced Lung Injury in Awake Sheep." *Eur. J. Clin. Invest.* 24(1994):229-235.

EMBASE Accession No. 2000083448. (2000).

Gladwin et al. "Inhaled Nitric Oxide Augments Nitric Oxide Transport on Sickle Cell Hemoglobin without Affecting Oxygen Affinity." *J. Clin. Invest.* 104.7(1999):937-945.

Greenburg et al. "Nitrosyl Hemoglobin Formation in-Vivo after Intravenous Administration of a Hemoglobin-Based Oxygen Carrier in Endotoxemic Rats." *Art. Cells, Blood Subs. Immobil. Biotechnol.* 23.3(1995):271-276.

Jia et al. "S-Nitrosohaemoglobin: A Dynamic Activity of Blood Involved in Vascular Control." *Nature.* 380.6571(1996):221-226.

Kruszyna et al. "Generation of Valency Hybrids and Nitrosylated Species of Hemoglobin in Mice by Nitric OXide Vasodilators." *Toxic. Appl. Pharm.* 94.3(1988):458-465.

Kruszyna et al. "Nitrite Conversion to Nitric Oxide in Red Cells and its Stabilization as a Nitrosylated Valency Hybrid of Hemoglobin." *J. Pharmacol. Exp. Ther.* 241.1(1987):307-313.

Kruszyna et al. "Red Blood Cells Generate Nitric Oxide From Directly Acting, Nitrogenous Vasodilators." *Toxic. Appl. Pharm.* 91.3(1987):429-438.

MEDLINE Accession No. 92296647. (1992).

Patel et al. "Biochemical Characterization of Human S-Nitrosohemoglobin." *J. Biol. Chem.* 274.22(1999):15487-15492.

Schreiber. "Protective Effect of Ascorbic Acid in High Altitude Hypoxia in the Rat." *Physiol. Res.* 41(1992):403-405.

Shvedova et al. "tert-Butyl Hydroperoxide/Hemoglobin-Induced Oxidative Stress and Damage to Vascular Smooth Muscle Cells." *Biochem. Pharmacol.* 57(1999):989-1001.

Sonoda et al. "An Assay Method for Nitric Oxide-Related Compounds in Whole Blood." *Ana. Biochem.* 247(1997):417-427.

The Merck Index, 12th Edition, Merck & Co., Inc., Whitehouse Station, N.J., p. 651, Item 3877 (1996).

TOXCENTER Accession No. 2002:618658. (1991).

Witdulsies, "Package Insert", 2 pages, Apr. 4, 1985.

Zaman et al. "S-Nitrosoglutathione Increases Cystic Fibrosis Transmembrane Regulator Maturation." *Biochem. Biophys. Res. Comm.* 284.1(2001):65-70.

* cited by examiner

US 8,871,506 B2

METHODS FOR TREATING CARDIO PULMONARY DISEASES WITH NO GROUP COMPOUNDS

RELATED APPLICATION

The present application is a divisional application of U.S. patent application Ser. No. 11/231,162, filed Sep. 20, 2005, which is a divisional application of U.S. patent application Ser. No. 10/069,114 (now U.S. Pat. No. 6,945,247), filed Feb. 28, 2002, which is a national stage application, filed under 35 U.S.C. §371, of PCT Application No. PCT/US00/20784, filed Aug. 18, 2000, which is a continuation-in-part of U.S. patent application Ser. No. 09/390,215 (now U.S. Pat. No. 6,314,956), filed Sep. 8, 1999, the contents of each of which are incorporated herein by reference in their entireties.

TECHNICAL FIELD

This invention relates to the treatment of respiratory, cardiac and blood disorders by delivery into the lungs of compound comprising NO substitute.

BACKGROUND OF THE INVENTION

Inhaled NO is used to treat elevated pulmonary pressures and pulmonary disorders associated with hypoxemia. This method of treatment provides distribution tightly matched to perfusion and local effect because of rapid trapping of inhaled NO by hemoglobin. Moreover, this method of treatment can be readily carried out by an anesthesiologist or a critical care physician who is used to administering gases. Side effects include reaction of NO with oxygen or reactive oxygen species to produce $NO_2$ or other toxic $NO_x$, the toxicity of which is manifested by inflammation, airway hyperactivity, hemorrhage, delay in clinical improvement, renal impairment or death, and reaction with oxyhemoglobin to interfere with its oxygen delivery function, e.g., by forming methemoglobin.

An alternative to inhaled NO gas is nebulized NO donor where the NO donor is present as solid particles or as particles of liquid. This alternative cannot fully avoid the $NO_2/NO_x$ toxicity problem associated with administration of NO but may produce longer lasting effects than inhaled NO. The distribution in the lungs is according to particle size and is not matched to perfusion so some NO donor deposits in places where it does not reach the blood or small airways. In the general case, these NO compounds have systemic smooth muscle relating effects greater than pulmonary effects, which limit usage for treating pulmonary disorders. Furthermore, this method is not as readily carried out by an anesthesiologist since anesthesiologists do not normally administer aerosols or powders. Moreover, some classes of NO donors have additional toxicities, that is, they possess toxicities that are unrelated to NO, but that are instead related to the group to which NO is attached or from which NO is generated. The disadvantages of administering nebulized NO donor are indicated to be meaningful by the fact that inhaled gaseous NO is approved for use over inhaled liquid or inhaled solid NO-releasing compound.

Use of inhaled NO and use of nitric oxide-releasing compounds inhaled as solids or liquids in an aerosol to treat pulmonary vasoconstriction and asthma are described in Zapol U.S. Pat. No. 5,823,180.

SUMMARY OF THE INVENTION

It is an object of an embodiment herein to provide selective pulmonary vasodilation and hypoxemia relieving effect by administration to the lungs of a gas without the toxicity associated with NO use.

It is an object of an embodiment herein to systemically deliver NO/SNO by administering into the lungs of a gas without interfering with the oxygen delivery function of hemoglobin. It also is an object of this embodiment to endow hemoglobin with improved and/or novel NO donor/releasing function.

It is an additional object to deliver NO/SNO without the toxicity (loss of specificity) associated with certain classes of NO donors.

One embodiment herein, denoted the first embodiment, is directed to a method for treating a pulmonary disorder associated with hypoxemia and/or smooth muscle constriction in the lungs and/or inflammation in the lungs in a patient having such disorder, said method comprising delivering into the lungs of said patient as a gas, a therapeutically effective amount of a compound having an NO group and having a hypoxemia relieving effect and a smooth muscle constriction relieving effect and/or an anti-inflammatory or inflammation defending effect with said NO group being bound in said compound so it does not form $NO_2$ or $NO_x$ in the presence of oxygen or reactive oxygen species at body temperature or exert systemic blood pressure compromising effect.

Another embodiment herein, denoted the second embodiment, is directed at a method of treating a cardiac disorder which is characterized by ischemia, pump failure and/or afterload increase in a patient having such disorder, said method comprising delivering into the lungs of said patient as a gas, a therapeutically effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature, whereby delivering into the lungs causes a systemic effect but does not compromise blood pressure.

Still another embodiment herein, denoted the third embodiment, is directed at a method of treating a blood disorder which is ameliorated by treatment with NO in a patient having said disorder, said method comprising delivering into the lungs of said patient as a gas, a therapeutically effective amount of a compound which reacts with cysteine in hemoglobin and/or dissolves in blood and has an NO group which is bound in said compound so that it does not form $NO_2$ or $NO_x$ in the presence of oxygen or reactive oxygen species at body temperature, whereby delivery into the lungs causes a desired systemic effect.

Still another embodiment herein, denoted the fourth embodiment, is directed to a method for treating a patient in need of improvement in tissue oxygenation or dilation of a blood vessel or inhibition of clotting (improved oxygenation, blood flow and/or thinning of blood), said method comprising providing in the patient a therapeutically effective amount of red blood cells loaded with nitrosylated hemoglobin, thereby to cause improved oxygen delivery or blood flow. The red blood cells loaded with nitrosylated hemoglobin can be provided in the patient by methods comprising, for example, (1) delivering into the lungs of the patient as a gas, a red blood cell loading effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature, as determined by measurement of nitrosylated hemoglobin in the blood; (2) infusing into the patient a solution of a compound which reacts preferentially with cysteine in hemoglobin and/or dissolves in blood and has an NO group which is bound in said compound so that it does not form $NO_2$ or $NO_x$ in the presence of oxygen or reactive oxygen species at body temperature, in an amount to load red blood cells in the patient with nitrosylated hemoglobin but insufficient to cause systolic blood pressure to drop below 90; and (3) transfusing into the patient blood containing red blood cells loaded with nitrosylated hemoglobin.

Exemplary of compound useful in the first, second and third embodiments and in (1) of the fourth embodiment is ethyl nitrite, which is also known as O-nitrosoethanol, used in gaseous form.

Advantages of embodiments herein include: (1), elimination of the toxicity caused by $NO_2/NO_x$ formation when NO is administered; (2), the option of administering the compound comprising NO group together with oxygen, without $NO_2/NO_x$ production; (3), no interference with the oxygen carrying function of hemoglobins since compounds administered herein do not react with heme in hemoglobin, so the physiological level in blood of methemoglobin will be less than 5% in blood; (4), NO bioactivity is preserved when the compound administered reacts with cysteine of hemoglobin; (5), is more efficient and selective at loading hemoglobin cysteine with NO group than free NO or nebulized nitric oxide-releasing compound liquid or solid; (6), the advantages associated with administration of a gas including matching ventilation to blood perfusion (ideal distribution), relatively localized lung effect compared to normal systemic administration of solutions and familiarity of anesthesiologists with the procedure whereby the administration is carried out; (6), less expensive administration since administration can be carried out using a ventilator rather than the very expensive machine used for administration of NO; (7), improved oxygenation, without rebound or with less rebound than when NO is administered; (8), some patients respond to administration of ethyl nitrite who do not respond to administration of NO; (9), cardiac output improves whereas this is not the case when NO is administered; (10), improvement in oxygen delivery without risk of hypotension occurring (the pulmonary effect is greater than the systemic effect but the systemic effect occurs in proportion to the oxygen requirement); and (11), loading the endogenous nitrosoglutathione pool. The methods of embodiments employing gaseous treating agent preserve the advantages of both NO gas inhalation and nebulized nitric oxide-releasing compound administration while minimizing the disadvantages associated with these known methods.

As used herein the term $NO_x$ means NO, $N_2O_3$, $N_2O_4$, $OONO^-$, OONO. and any products of their interaction or their reaction with NO or $NO_2$.

As used herein the term reactive oxygen species is singlet oxygen; superoxide, hydrogen peroxide or hydroxyl radical.

As used herein the term hypoxemia means low blood oxygen content compared to normal, i.e., a hemoglobin saturation less than 95% and a $Pa_{O2}$ less than 90 in arterial blood in someone breathing room air.

As used herein the term $Pa_{O2}$ means the partial pressure of oxygen in gases in arterial blood.

As used herein the term "red blood cells loaded with nitrosylated hemoglobin" means red blood cells containing from 100 nanomolar to 10 micromolar nitrosylated hemoglobin, above baseline, preferably from 100 nanomolar to 1 micromolar above baseline. In the red blood cells, the nitrosylated hemoglobin is in equilibrium with nitrosoglutathione.

As used herein the term "rebound" is used to mean lowering in blood oxygen level or increase in pulmonary artery pressure or resistance after increased blood oxygen level or decreased pulmonary vascular pressure/resistance is obtained by treatment, by at least 10%, when used in relation to blood oxygen levels or pulmonary hypertension, and in general means decrease from improvement after treatment.

Other embodiments are as follows:

One additional embodiment, denoted the fifth embodiment, is directed to red blood cells loaded with nitrosylated hemoglobin, outside the body.

Another additional embodiment, denoted the sixth embodiment, is directed to a method of screening for drugs that increase the level of nitrosoglutathione in airway lining fluid, comprising administering a putative drug in gas form into the lung of a model animal, sampling airway lining fluid from the animal, and assaying for nitrosoglutathione in the sample obtained by sampling.

DETAILED DESCRIPTION OF THE INVENTION

Figure 1:
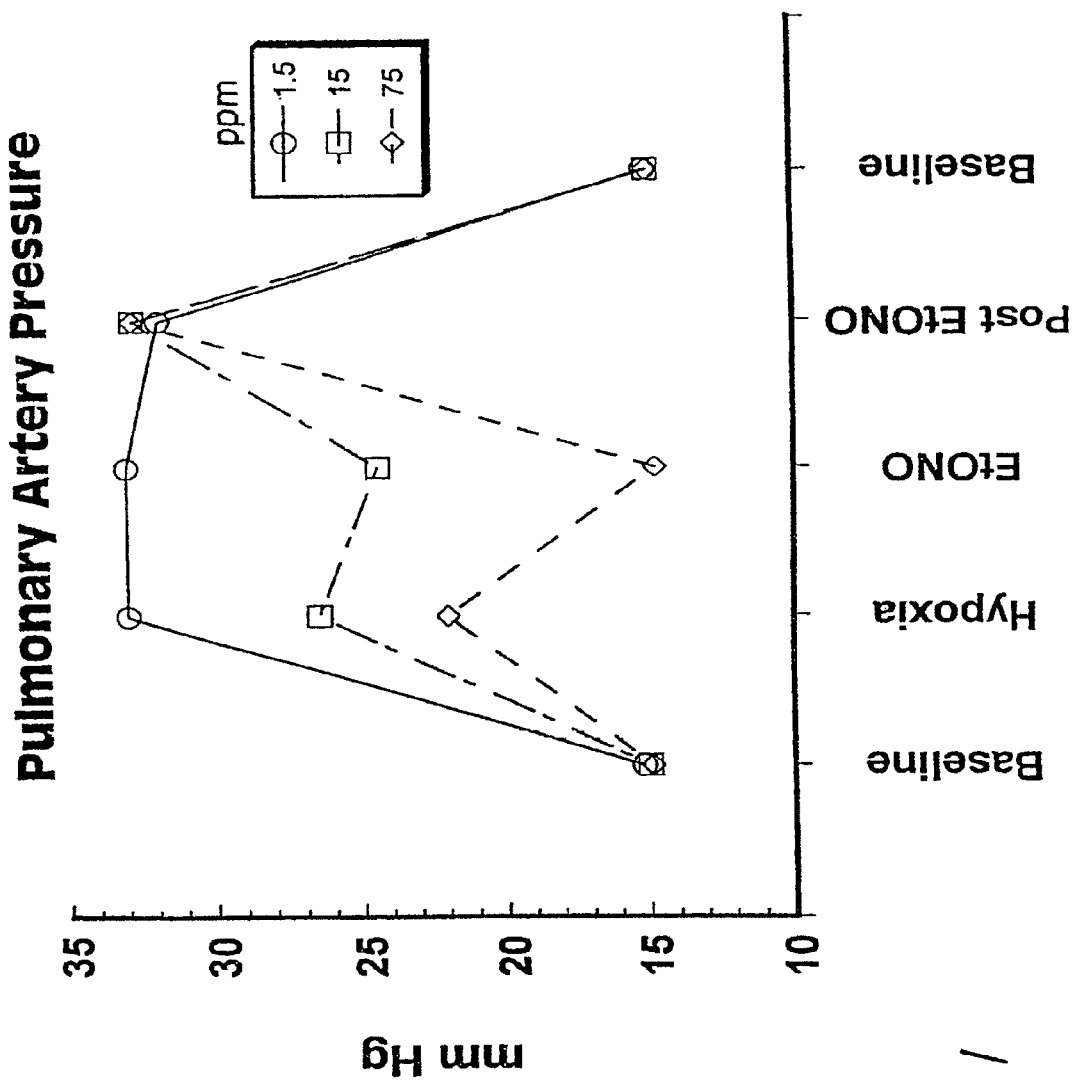
FIG. 1 depicts graphs of pulmonary artery pressure for three doses of ethyl nitrite gas and shows results of Example I.

We turn now to the method for treating a pulmonary disorder associated with smooth muscle constriction in lungs and/or hypoxemia and/or inflammation in the lungs in a patient having such disorder, said method comprising delivering into the lungs of said patient as a gas, a therapeutically effective amount of a compound having an NO group and having a hypoxemia relieving effect and a smooth muscle constriction relieving effect and an anti-inflammatory or inflammation defending effect with said NO group being bound in said compound so it does not form $NO_2$ or $NO_x$ in the presence of oxygen or reactive oxygen species at body temperature or exert systemic blood pressure compromising effect.

The pulmonary disorders treatable by this method include, for example, pulmonary hypertension including persistent pulmonary hypertension in human babies and primary and secondary pulmonary hypertension in human adults, acute respiratory distress syndrome (ARDS), asthma, cystic fibrosis and respiratory failure.

Pulmonary hypertension is associated with smooth muscle constriction in the lungs and it can be associated with hypoxemia.

ARDS is a radiographic manifestation associated with low oxygen content in blood and typically is also associated with elevated pulmonary pressures. Oxygen free radical injury contributes to the pathophysiology. Free NO can aggravate the injury by reacting with oxygen free radicals to form toxic products of reaction (i.e., they damage tissues), but the compounds administered herein do not have this effect because they do not react with oxygen free radicals. Inhaled NO has been showing to result in increased morbidity and mortality. This with disorder is associated with hypoxemia and it can be associated with smooth muscle constriction in the lungs.

Asthma is associated with smooth muscle constriction in the lungs and can be associated with hypoxemia.

Cystic fibrosis is associated with smooth muscle construction in the lungs and can be associated with hypoxemia.

We turn now to the compounds having an NO group and having a hypoxemia relieving and a smooth muscle constriction relieving effect and an anti-inflammation or inflammation defending effect with said NO group being bound in said compound. These compounds are less reactive with oxygen or with oxygen free radicals at body temperature than NO and are more potent antimicrobials than NO. These compounds include, for example, those having the formula RX—$NO_y$, where R is either not present or is hydrogen/proton or $C_1$-$C_7$-alkyl and X is an oxygen, sulfur, nitrogen or metal selected, for example, from the group consisting of iron, copper, ruthenium and cobalt atoms or an alkyl or alkenyl or alkylthio or alkenylthio group containing from 1 to 7, e.g., 1 to 6, carbon atoms which is straight chain or branched, $CF_3$— and $CF_3S$—, and y is 1 or 2, excluding nitrogen dioxide and $NO_x$.

Specific treating agents for use herein include, for example, ethyl nitrite (which is used in examples herein), methyl nitrite, tert-butyl nitrite, isoamyl nitrite, trifluoronitrosomethane ($CF_3NO$), $CF_3SNO$, $CH_3SNO$, $CH_2$=CHSNO, $CH_2$=$CHCH_2SNO$, $ONSCH_2$—$CH_2$—$CH_2SNO$ and $CH_3CH_2CH_2SNO$. Alkyl nitrites can be prepared as described in Landscheidt et al. U.S. Pat. No. 5,412,147. Ethyl nitrite is available commercially, e.g., diluted in ethanol. $CF_3NO$ is a commercial product or can be made by treatment of $CF_3I$ with $NO^-$ as described in J. Phys. Chem. 100, 10641 (1996). Aliphatic thionitrites, i.e., compounds of the form RSNO where R describes an alkyl or alkenyl or hydrogen moiety, can be prepared by treatment of the corresponding thiol with a source of $NO^+$ including, but not limited to, one or more of the following: tert-butyl nitrite, ethyl nitrite, nitrosonium tetrafluoborate ($NOBF_4$), nitrosonium perchlorate ($NOClO_4$), nitrosonium hydrogen sulfate ($NOHSO_4$), nitrosonium hydrogen phosphate ($NOH_2PO_4$), or HCl-acidified solutions of sodium nitrite.

We turn now to the administration of these compounds. Those that are normally gases are readily administered diluted in nitrogen or other inert gas and can be administered in admixture with oxygen. Those that are not normally gases are converted to gas for administration and are administered diluted as in the case of the NO-containing compounds that are normally gases. The compounds should not have a boiling point such that the temperature required to maintain them as gases in diluted form would harm the lungs and preferably would not condense in the lungs.

Dilution, for example, to a concentration of 1 to 100 ppm is typically appropriate.

The diluted gas is readily delivered into the lungs, using a ventilator which is a conventional device for administering gases into the lungs of a patient. A tube attached to the device passes the gas into the lungs at a rate and pressure consistent with maintaining a $Pa_{O2}$ of 90 mm Hg. Time periods of administration typically range from 1 minute to two or more days, and administration is carried out until symptoms abate. Administration can also be carried out using a face mask.

As indicated above, a therapeutically effective amount is administered. This is a hypoxemia relieving effective and smooth muscle constriction relieving and an anti-inflammatory or inflammation defending (against) effective amount. Administration is carried out for as long as symptoms ameliorate. The dosage will vary from patient to patient. Upon administration, results are noted with variation in dosage and then the dosage is preferably used where the best results are achieved. The most effective dosage can be lower than some of the dosages tried; thus, if after increases in dosage are tried, an increased dosage provides less improvement, then return to the more effective lower dose is indicated. The ideal dosage matches ventilation to perfusion.

Ethyl nitrite is readily delivered to the patient in gaseous form by bubbling $N_2$ or $O_2$ through a Milligan gas diffuser containing ethyl nitrite diluted in ethanol (e.g., from 0.00125 to 0.5% ethyl nitrate in ethanol (v/v), preferably from 0.0025 to 0.125% ethyl nitrite in ethanol (v/v)), e.g., at a flow rate of 0.5 liters/min to 1.5 liters/min, to produce $N_2$ or $O_2$ containing ethyl nitrite and introducing this into the ventilation system by mixing the output from the ventilator at a total of 5 to 15 liters/min with the $N_2$ or $O_2$ containing ethyl nitrite, for example, to produce a concentration of 1 to 100 ppm ethyl nitrite in the resulting gas, and delivering this to the patient at a rate and pressure to maintain $Pa_{O2}$ at 90 mm Hg or to improve $Pa_{O2}$ or to decrease pulmonary vascular resistance. The concentration of ethyl nitrite gas administered is proportional to the flow rate of $N_2$ or $O_2$ and the concentration of ethyl nitrite liquid in ethanol.

An advantage for treatment using ethyl nitrite compared to administration of NO is that no new equipment is needed for ethyl nitrite administration whereas a machine costing tens of thousands of dollars is required to administer NO. Thus, it is less expensive to administer ethyl nitrite than it is to administer NO.

Furthermore, use of ethyl nitrite improves oxygenation without the toxic $NO_2$ and $NO_x$ formation associated with administration of NO and without the rebound to lower oxygen levels or higher pulmonary pressures once administration is stopped that is characteristic of what occurs on administration of NO.

Furthermore, administration of ethyl nitrite stops cardiac output from going down in disease. This is not the case for administration of NO.

Furthermore, administration of ethyl nitrite is better than administration of NO in raising the level of NO bound to cysteine in hemoglobin.

While not being bound by the mechanism stated, it is considered that nitrosoglutathione loading (that is increase in nitrosoglutathione in airway lining fluid) is the basis for the improved oxygenation without rebound to lower levels after administration is stopped and the stopping of cardiac output from going down. Administration of ethyl nitrite causes glutathione loading whereas administration of NO does not.

Another advantage for ethyl nitrite compared to NO is that, unlike NO, it can be administered in oxygen. NO is not stable in oxygen and has to be given in a nitrogen base which dilutes inspired $O_2$ concentration. Because of this, a patient that is given inhaled NO gas cannot be given a higher concentration of $O_2$ than 95%. In contrast, ethyl nitrite can be given with 100% $O_2$ and does not dilute oxygen concentration at all, so a patient given inhaled ethyl nitrite can be given a higher concentration of oxygen than a patient given inhaled NO. Therefore, in the treatment of persistent pulmonary hypertension, babies that required 100% oxygen can be continued on 100% oxygen when ethyl nitrite is administered whereas the final inspired concentration of oxygen drops when NO is administered.

When NO is used to treat babies with persistent pulmonary hypertension, the treatment is expensive, there is a need to monitor $NO_2$ and $NO_x$ formation or pulmonary vascular resistance, methemoglobin is formed, and there is rebound in every case of improved blood oxygen levels. With NO, there is hemodynamic collapse in 25% of patients if something further is not done. There is an advantage for ethyl nitrite administration in all these cases and there is not the hemodynamic collapse problem or rebound. Moreover, some babies respond to ethyl nitrite that do not respond to administration of NO. Furthermore, cardiac output improves with ethyl nitrite administration but not with administration of NO.

We turn now to the method for treating a cardiac disorder which is characterized by ischemia, pump failure and/or afterload increase in a patient having such disorder, said method comprising delivering into the lungs of said patient as a gas, a therapeutically effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature.

The cardiac disorders treatable by this method include angina, myocardial infarction, heart failure and hypertension.

In the case of treating hypertension, it is required that the NO-group containing compound administered is one that reacts with cysteine in hemoglobin as discussed below, e.g., ethyl nitrite, and that a thiol also be administered systemically or by inhaled route to promote systemic release of NO from binding to cysteine of hemoglobin. In the cases of treating other cardiac disorders, where the NO-containing compound administered is one that reacts with cysteine in hemoglobin, e.g., ethyl nitrite, it is an option that a thiol also be administered systemically (e.g., intravenously or orally or nebulized) or by inhaled route to cause systemic release of NO from binding to cysteine of hemoglobin. Suitable thiols include, for example, N-acetylcysteine (dosage, e.g., ranging from 50 to 200 mg/kg intravenously or 600 mg three times a day orally or nebulized according to the FDA approved PDR dosage, with a preferred route of administration being intravenous or nebulized), glutathione (dosage, e.g., ranging from 50 to 200 mg/kg with preferred route of administration being intravenous), and cysteinylglycine (dosage, e.g., ranging from 50 to 200 mg/kg with preferred route of administration being intravenous).

We turn now to the compounds which react with cysteine in hemoglobin and/or dissolve in blood and have an NO group which is bound in said compounds so it does not form $NO_2$ or $NO_x$ in the presence of oxygen or reactive oxygen species at body temperature, for use in the method herein for treating cardiac disorders. These compounds include, for example, those having the formula RX—$NO_y$ described above and the species of this class recited above (ethyl nitrite is used in working examples hereinafter); as indicated above, those compounds that are not normally gases, i.e., not gases at room and body temperature, are converted to gas for administration.

The concentrations of NO-containing compound and methods of administration applicable to the method of treating a pulmonary disorder described above are applicable to the method herein for treating cardiac disorders.

As indicated above, a therapeutically effective amount of NO-containing compound in gas form is administered in the method herein for treating cardiac disorders. This is a chest pain reducing effective amount for angina, a heart failure resolving effective amount for myocardial infarction, a pulmonary pressure reducing and peripheral vascular resistance reducing effective amount for heart failure and a blood pressure lowering effective amount for hypertension. The most effective dosage will vary from patient to patient, so it is preferred in each case to try a plurality of dosages and then to utilize dosage where the best results were achieved.

For administration of ethyl nitrite for treating cardiac disorders, the same concentrations and methods of administration are applicable as are described above for treating pulmonary disorders.

When ethyl nitrite is administered, there is improvement without rebound.

We turn now to the method for treating a blood disorder in a patient having said disorder, said method comprising delivering into the lungs of said patient as a gas, a therapeutically effective amount of a compound which reacts with cysteine in hemoglobin and/or dissolves in blood and has an NO group which is bound in said compound so that it does not form $NO_2$ or $NO_x$ in the presence of oxygen or reactive oxygen species at body temperature.

The blood disorders are those ameliorated by treatment with NO or related molecules, i.e., where NO would change the shape of red blood cells to normal or restore their function to normal or would cause dissolution of blood or blood platelet clots. These include sickle cell disease and clotting disorders including disseminated intravascular coagulation (DIC), heart attack, stroke, and Coumadin induced clotting caused by Coumadin blocking protein C and protein S.

We turn now to the compounds which react with cysteine in hemoglobin and/or dissolve in blood and have an NO group which is bound in said compound so that it does not form $NO_2$ or $NO_x$ in the presence of oxygen or reactive oxygen species at body temperature, for use in the method herein for treating blood disorders. These compounds are the same as those recited for treating cardiac disorders and include, for example, those having the formula RX—$NO_y$ described above and the species of this class recited above (ethyl nitrite is used in working examples herein); as indicated above, those compounds that are not normally gases, are converted to gas form for administration.

The concentrations of NO-containing compound and methods of administration applicable to the method for treating a pulmonary disorder described above are applicable to the method herein for treating blood disorders.

As indicated above, a therapeutically effective amount of NO-containing compound in gas form is administered in the method herein for treating blood disorders. This is a red blood cell shape restoring and/or red blood cell function restoring effective amount for sickle cell disease and a clot dissolving and/or clot formation preventing amount for clotting disorders. The most effective dosage will vary from patient to patient, so it is preferred in each case to try a plurality of dosages and then to utilize the dosage where the best results were achieved.

Where the NO-group containing compound administered for treating a blood disorder is one that reacts with cysteine in hemoglobin, it is advantageous to administer the NO-group containing compound in conjunction with a thiol to cause systemic release of NO from binding to cysteine of hemoglobin. Suitable thiols, dosages and routes of administration are those described in conjunction with thiols above.

For administration of ethyl nitrite for treating blood disorders, the same concentrations and methods of administration are applicable as are described above for treating pulmonary disorders.

We turn now to the embodiment herein directed to a method for treating a patient in need of improvement of tissue oxygenation, dilation of a blood vessel or inhibition of clotting, said method comprising providing in the patient a therapeutically effective amount of red blood cells loaded with nitrosylated hemoglobin, thereby to cause improved oxygenation or blood flow.

This method finds applicability, for example, in treating patients affected with sickle cell disease and ischemic disorders, e.g., angina, heart attack or stroke.

As indicated above, in one case, the red blood cells loaded with hemoglobin are provided in the patient by a method comprising delivering into the lungs of the patient as a gas, a red blood cell loading effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature, as determined by measurement of nitrosylated hemoglobin in blood. This case will be referred to hereinafter as the first case of the fourth embodiment.

We turn now to the compounds which react with cysteine in hemoglobin and/or dissolve in blood and have an NO group which is bound in said compounds so it does not form $NO_2$ or $NO_x$ in the presence of oxygen or reactive oxygen species at body temperature, for use in the method herein for the first case of the fourth embodiment. These compounds are the same as those recited for treating cardiac disorders and for treating blood disorders and include, for example, those having the formula $RX-NO_y$ described above and the species of this class recited above, including ethyl nitrite; as indicated above, those compounds that are not normally gases, are converted to gas for administration.

The concentrations of NO-containing compound and methods of administration applicable to the method of treating a pulmonary disorder described above are applicable to the method herein for treating the first case of the fourth embodiment.

A therapeutically effective amount for the first case of the fourth embodiment is an oxygen delivery or blood flow increasing or blood thinning effective amount.

Where the NO-group containing compound administered for treating the first case of the fourth embodiment is one that reacts with cysteine in hemoglobin, it is advantageous to administer the NO-group containing compound in conjunction with a thiol to cause systemic release of NO from binding to cysteine of hemoglobin. Suitable thiols, dosages and routes of administration are those described in conjunction with thiols above.

For administration of ethyl nitrite for treating the first case of the fourth embodiment, the same concentrations and methods of administration are applicable as are described above for treating pulmonary disorders.

Measurement of nitrosylated hemoglobin in the blood can be carried out as described in Jia, L., et al., Nature; Vol. 380, 221-226 (1996).

As further indicated above, in another case, the red blood cells loaded with hemoglobin are provided in the patient by a method comprising infusing into the patient a solution of a compound which reacts with cysteine in hemoglobin and/or dissolves in blood and has an NO group which is bound in said compound so that it does not form $NO_2$ or $NO_x$ in the presence of oxygen or reactive oxygen species at body temperature in an amount to load red blood cells in the patient with nitrosylated hemoglobin but insufficient to cause systolic blood pressure to drop below 90. The limitation about blood pressure is included because ethyl nitrite when infused as a liquid, causes a drop in blood pressure. This case will be referred to hereinafter as the second case of the fourth embodiment.

The compounds for use in the second case of the fourth embodiment can be the same as those used in the first case of the fourth embodiment but unlike in the first case of the fourth embodiment, they are infused in liquid form instead of being administered as gases. The liquid form can be obtained by administering the compounds dissolved in a solvent, e.g., a protic solvent such as an alcohol. Ethyl nitrite dissolved in ethanol to provide an ethanol solution containing 0.00125 to 0.5 percent (v/v) ethyl nitrite is a preferred agent for the second case of the fourth embodiment and the solution more preferably contains 0.0025 to 0.125 percent ethyl nitrite (v/v).

A therapeutically effective amount for the second case of the fourth embodiment is an oxygenation improving or blood flow improving effective amount.

Administration of the solution of compound that reacts with cysteine in hemoglobin and/or dissolves in blood is preferably carried out intravenously.

Where the NO-group containing compound administered for treating is one that reacts with cysteine in hemoglobin, it is advantageous to administer the NO-group containing compound in conjunction with a thiol to cause systemic release of NO from binding to cysteine of hemoglobin. Suitable thiols, dosages and routes of administration including intravenously, orally and nebulized, are those described in conjunction with thiols above.

As still further indicated above, in another case, the red blood cells loaded with hemoglobin are provided in the patient by a method comprising transfusing into the patient blood containing red blood cells loaded with nitrosylated hemoglobin. The blood containing red blood cells loaded with hemoglobin can be obtained by incubating blood for 1 minute to 1 hour, e.g., 1 minute to 30 minutes, at 25 to 37° C. with a compound which reacts with cysteine in hemoglobin and/or dissolves in blood and has an NO group which is bound in said compound so that it does not form $NO_2$ or $NO_x$ in the presence of oxygen of reactive oxygen species at body temperature. The compounds can be the same as those described above for compound that reacts with cysteine and/or dissolves in blood and has an NO group which is bound in the compound so that it does not form $NO_2$ or $NO_x$ in the presence of oxygen or reaction oxygen species at body temperature. The incubation is preferably carried out by incubating blood with an ethanol solution of ethyl nitrite containing from 0.00125 to 0.5% (v/v) ethyl nitrite, preferably containing from 0.0025 to 0.125% (v/v) ethyl nitrite, with the amount of ethyl nitrite to hemoglobin present for incubation ranging from 1:1000 to 10:1, preferably from 1:100 to 10:1. This case will be referred to hereinafter as the third case of the fourth embodiment.

Preferably, thiol is co-administered for the third case of the fourth embodiment. Suitable thiols, dosage and routes of administration are those described in conjunction with thiol administration above.

A therapeutically effective amount of red blood cells loaded with nitrosylated hemoglobin is 0.1 to 3 units of blood having nitrosylated hemoglobin increased 0.1 to 1 micromolar over baseline or equivalent.

Administration is preferably carried out by transfusion.

We turn now to the embodiment herein which is red blood cells loaded with nitrosylated hemoglobin outside the body. These are readily made as described in the third case of the fourth embodiment.

We turn now to the method herein for screening for drugs that increase the level of nitrosoglutathione in airway lining fluid, comprising administering the drug in gas form into the lung of a model animal, sampling airway lining fluid and assaying for nitrosoglutathione in the sample obtained by sampling. Model animals include, for example, neonatal pigs, guinea pigs, rats and dogs. A sample of airway lining fluid is readily obtained by bronchoscopy. Assay for nitrosoglutathione in sample is readily carried out, for example, as described in Gaston, B., et al., PNAS, Vol. 90, 10957-10961 (1993). A level indicating increase of nitrosoglutathione at least 50% above baseline indicates a candidate for a drug for increasing level of nitrosoglutathione in airway lining fluid of mammals including humans.

The invention herein is illustrated by, but not limited by, the following working examples.

Example I

The experiment was carried out using a pig model of pulmonary hypertension as follows:

Mixed strain two-three weeks old piglets were utilized. Initial anesthetic induction was by inhaled halomethane 5%, reduced to 2% when the animal was stable. A bolus of 20 µg/kg of fentanyl and 0.2 mg/kg of acepromazine was given after tracheostomy surgery and insertion of a jugular venous line, followed by a continuous fentanyl infusion of 10 µg/kg/hr. An incision in the right side of the neck allowed the insertion of a catheter through the external jugular vein into the right atrium, through which maintenance iv. fluid of 30 mL/kg/hr of 5% glucose was infused. A catheter was placed in the carotid artery for measurement of systolic arterial pressure (SAP). After the tracheostomy, halothane was discontinued, assisted ventilation was started, and paralysis was obtained using pancuronium bromide (0.1 mg/kg) every 45 minutes. Further bolus doses of fentanyl (5-10 µg/kg) were administered as necessary. Through a left thoracotomy, a 6- or 8-mm ultrasound flow probe (Transonic Inc., Rochester, N.Y.) was placed around the pulmonary artery for measurement of cardiac output and a 4- to 6-mm probe was placed around the ductus arteriosus. A 22-gauge catheter was inserted into the root of the pulmonary artery through a purse string suture for the continuous measurement of pulmonary artery pressure (PAP). The systemic and pulmonary catheters were connected to pressure transducers and together with the ECG signal, displayed on a neonatal monitor (Model 78833B, Hewlett Packard, Waltham, Mass.). Systemic oxygen saturation ($SaO_2$) was measured using a subcutaneous pulse oximeter (N200, Nellcor Inc., Hayward, Calif.). A continuous infusion of bicarbonate (15 mEq/100 mL of i.v. fluid) was given to prevent severe acidosis during periods of hypoxia. Cardiac output was determined from measurements of the calibrated ultrasonic flow probe.

After this instrumentation, the animal was allowed to rest for 20 minutes to ensure stability, which was defined as less than 5% variation in heart rate, SAP, and PAP over a 5-minute period, and thereafter hypoxia was induced by reduction of the inspired oxygen concentration to 10 to 14% to produce a target $SaO_2$ of 35 to 45%. After induction of hypoxia, a stable hypoxic baseline was obtained (2 minutes). An arterial blood specimen was obtained for the measurement of blood gases and methemoglobin.

Ethyl nitrite (EtONO) was then administered according to a computer-generated random sequence in doses of 1.5, 15 or 75 ppm by changing the EtONO concentration (at a fixed flow rate), maintaining the fractional inspired oxygen saturation ($FiO_2$) at the same level. The ethyl nitrite was administered with nitrogen by introducing nitrogen ethyl nitrite admixture into the ventilation system by mixing the output from the ventilator with said admixture. The ethyl nitrite nitrogen admixture was generated by bubbling nitrogen through a Milligan gas diffuser (Fisher Scientific) containing ethyl nitrite diluted in ethanol (0.075% (v/v) ethyl nitrate) at a flow rate of 0.6 liters/min to produce nitrogen containing ethyl nitrite which is then blended in the ventilator with the incoming gas for a flow rate of 6 liters/min. The concentration of ethyl nitrite in the gas to be administered is directly proportional to the flow of nitrogen into the Milligan gas diffuser and/or the concentration of ethyl nitrite in ethanol. Measurements were obtained at each dose when there were no further changes in PAP, $SaO_2$, SAP, or cardiac output, and the signals were recorded for 1 minute. At this point, EtONO administration was discontinued. Post EtONO data was from samples 4 minutes after EtONO discontinuance and final baseline samples were taken when the parameter being measured stabilized (about 4 minutes after the post EtONO sample). This procedure was repeated until all doses of EtONO had been administered. If an animal experienced significant hypotension (systolic arterial pressure decreasing to less than 60% of hypoxic baseline), the hypoxia was terminated, and the animal was allowed to recover before reintroducing hypoxia.

The physiologic parameters of interest were acquired through a personal computer (Dell 486/33, Dell Computer Corporation, Richmond Hill, Ontario, Canada) using an analog-to-digital converter (DT 2801, Data Translation Inc., Marborough, Mass.). Software for acquisition analysis was written using Asyst Scientific Software System (Macmillan Software Co., New York, N.Y.). With this software, continuous acquisition of the measured parameters was performed for a 2-minute period at baseline, and a 1-minute period after stability during each hypoxic EtONO exposure. The computer-generated averages of the measured parameters were then utilized for subsequent analyses. The time responses of the changes in PAP were similarly analyzed using the average values for 1 second for the PAP to determine the time response of the change in PAP compared to baseline. All signals were acquired at 24 Hz. In order to compensate for sampling delay time for the analyzer which was approximately 5 seconds, initiation of the response was considered to be 5 seconds before the initial indication that the results of the appropriate dose had been measured by the analyzer (measured by GC mass spectral analysis using a model system). Cardiac Index was calculated as cardiac output divided by the animal's weight in kilograms. Pulmonary Vascular Resistance (PVR) was calculated as mean PAP divided by cardiac index. Pulmonary Artery Flow (FIG. 3) was measured using a Doppler flow probe.

Results are shown in FIGS. 1-6.

FIG. 1 depicts graphs of PAP in mm Hg for the three concentrations of EtONO administration with data points at baseline, hypoxia (stable hypoxic baseline), EtONO (when no further changes in PAP for one minute), post EtONO (4 minutes after EtONO discontinuance) and baseline (when PAP normalized, approximately 4 minutes after post EtONO data). The data shows hypoxia increased PAP and that EtONO administration reverses hypoxic pulmonary vasoconstriction.

Figure 2:
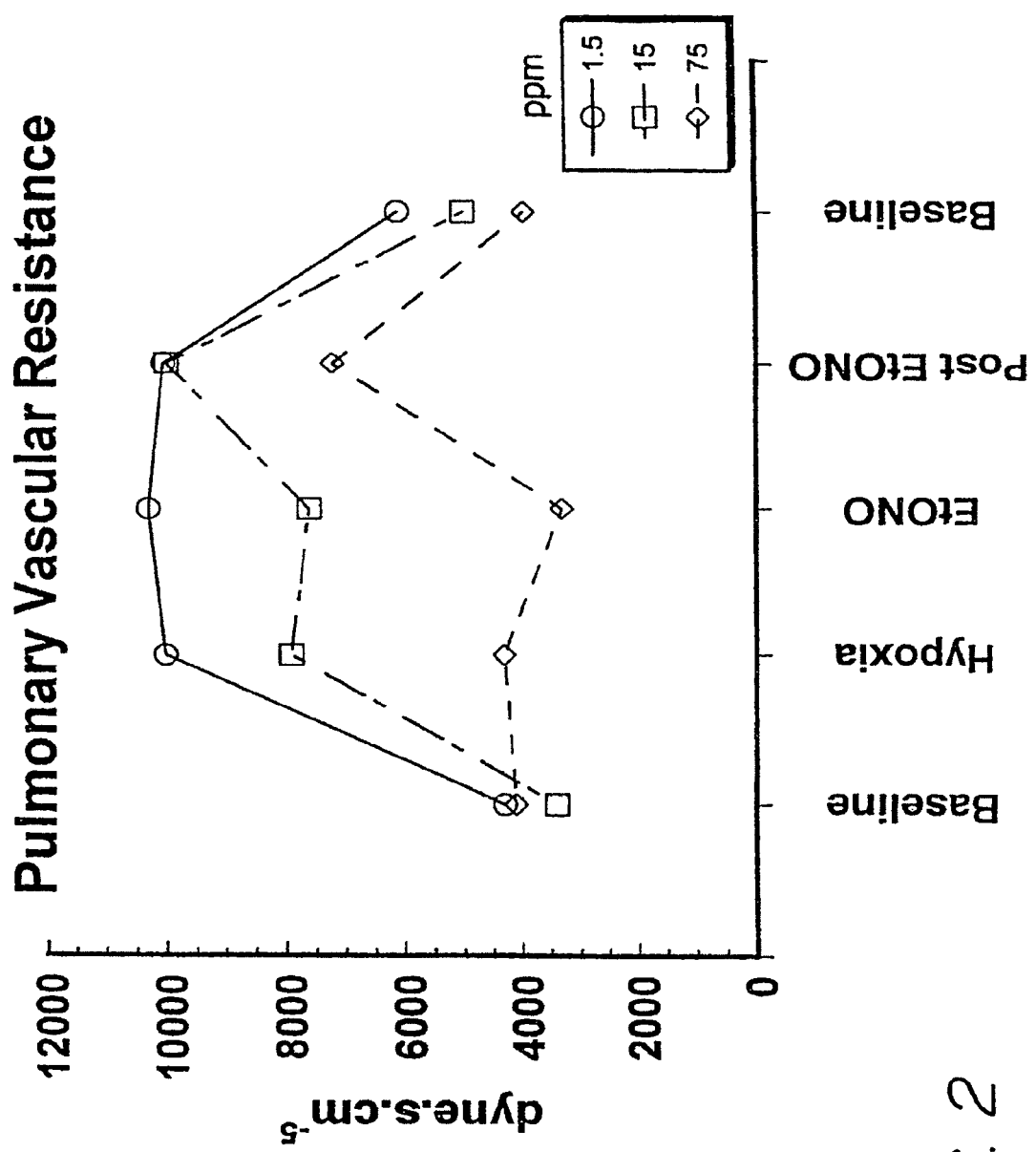
FIG. 2 depicts graphs of pulmonary vascular resistance for three doses of ethyl nitrite gas and shows results of Example I.

FIG. 2 depicts graphs of PVR in dynes×5×cm$^{-1}$ for the three concentrations of EtONO administration with data points at the same stages as for FIG. 1. The data shows hypoxia increased PVR and that EtONO administration restores PVR toward initial baseline.

For FIGS. 1 and 2, any progressive loss of effect of hypoxia on pulmonary vascular hemodynamics is consistent with a positive effect of EtONO.

Figure 3:
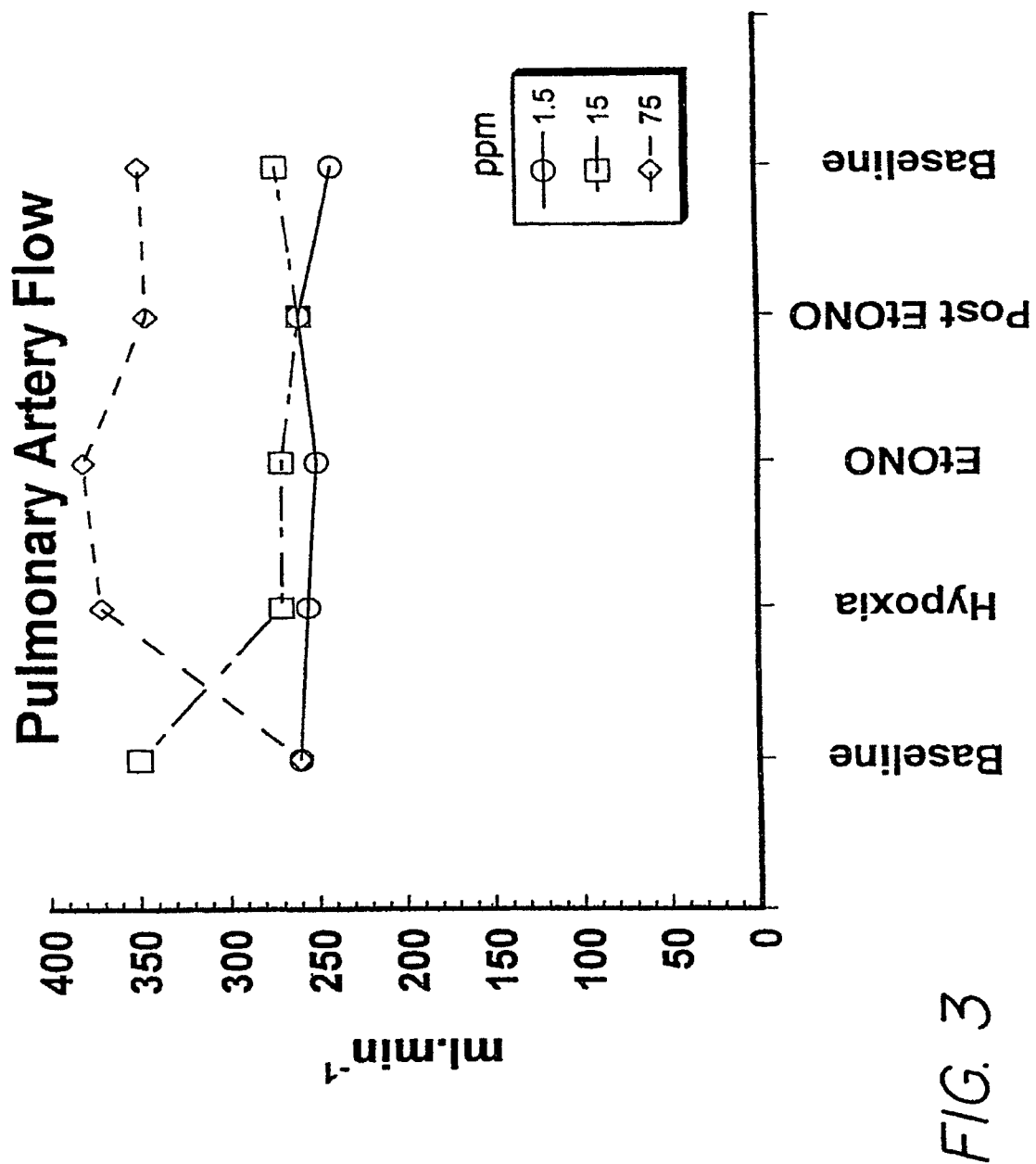
FIG. 3 depicts graphs of pulmonary artery flow for three doses of ethyl nitrite gas and shows results of Example I.

FIG. 3 depicts graphs of pulmonary artery flow in ml/min for the three concentrations of EtONO administration with data points at the same stages as for. The data shows EtONO administration increases pulmonary artery flow at 75 ppm.

Figure 4:
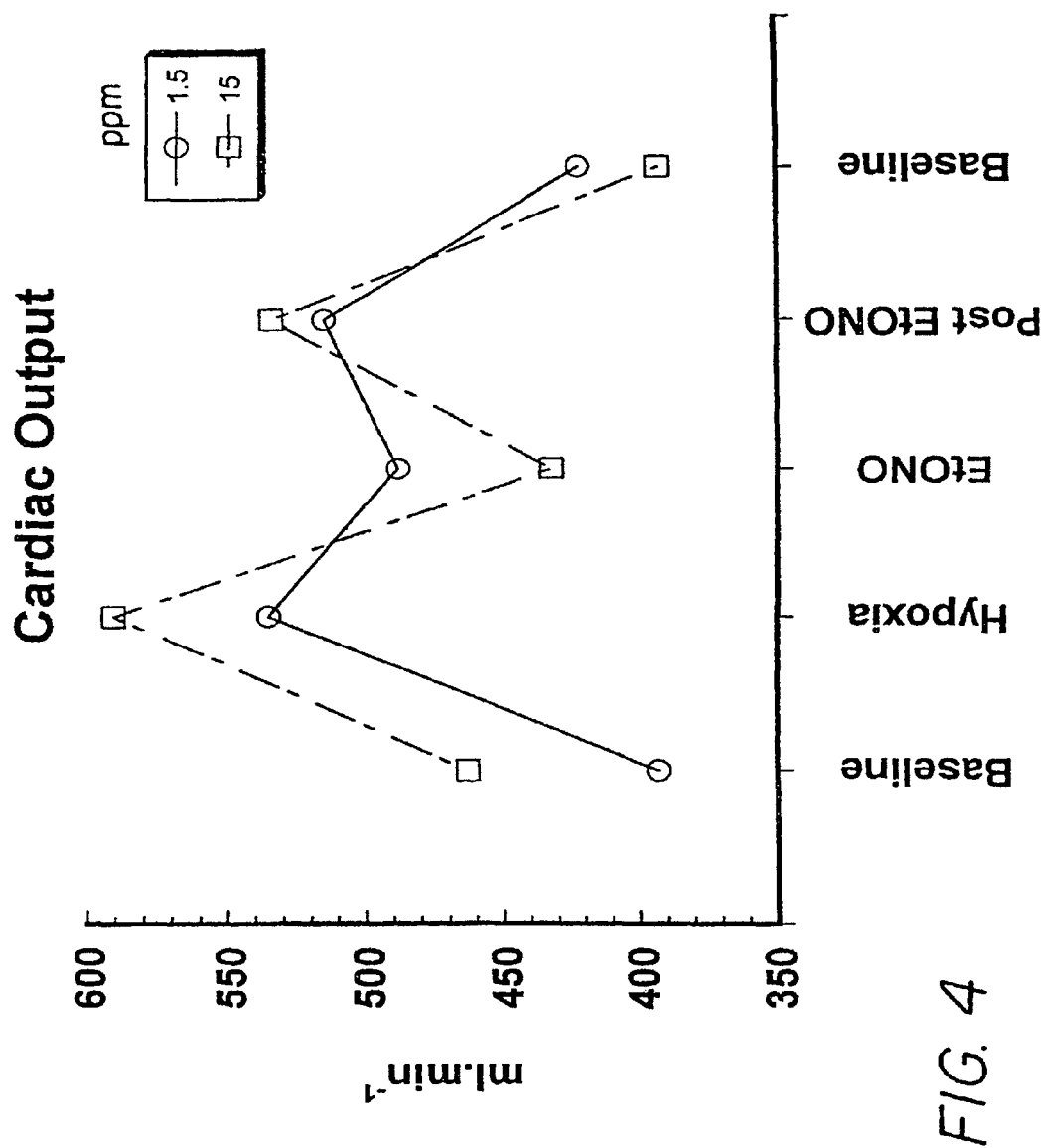
FIG. 4 depicts graphs of cardiac output for two doses of ethyl nitrite gas and shows results of Example I.

FIG. 4 depicts graphs of cardiac output in ml/min for two concentrations of EtONO administration with data points at the same stages as for FIG. 1. The data shows that EtONO administration tends to normalize the hypoxia induced increase in cardiac output.

Figure 5:
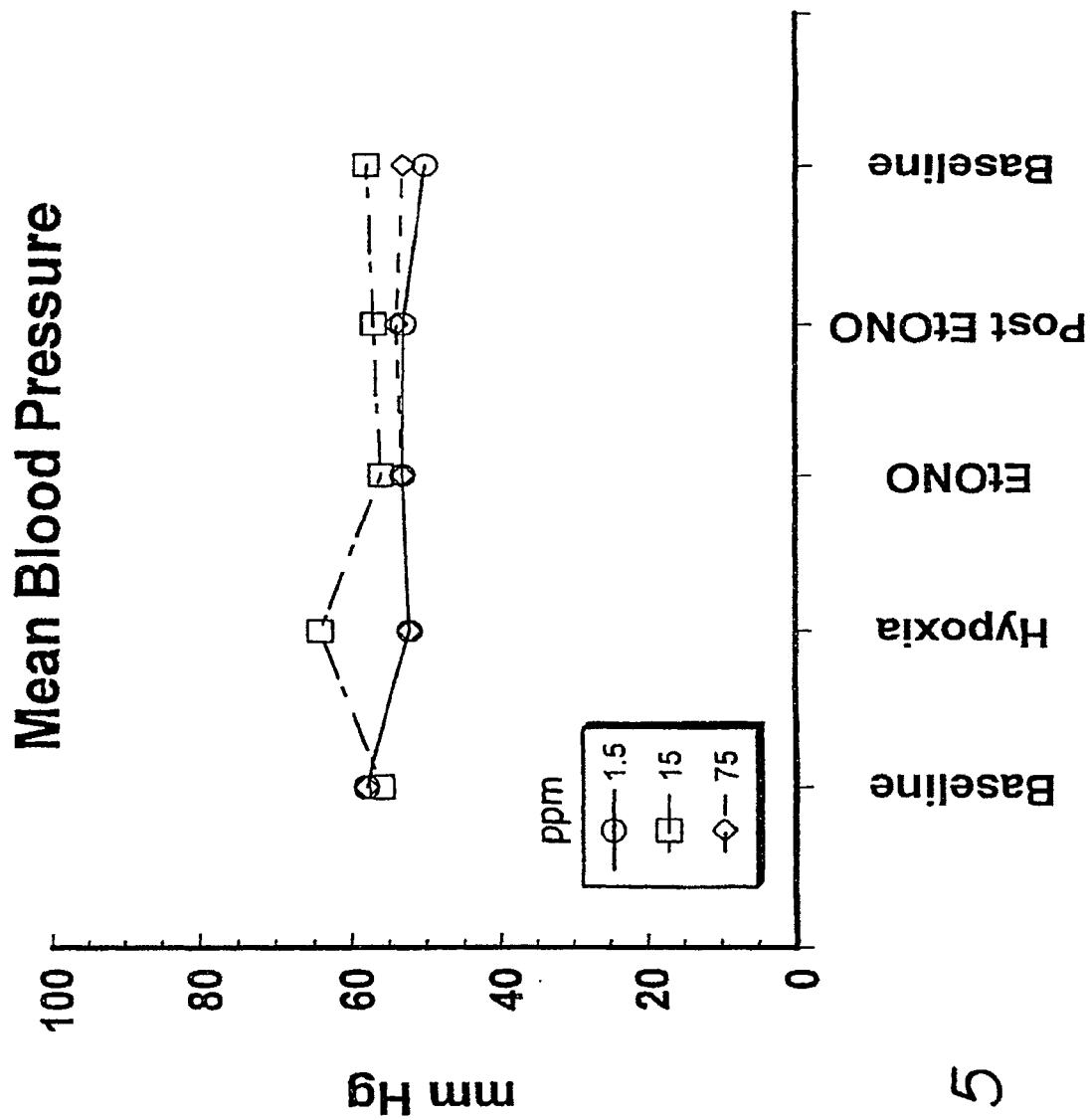
FIG. 5 depicts graphs of mean blood pressure for three doses of ethyl nitrite gas and shows results of Example I.

FIG. 5 depicts graphs of mean blood pressure in mm Hg for three concentrations of EtONO administration with data points at the same stages as for FIG. 1. The data shows that EtONO administration has no effect on blood pressure.

Figure 6:
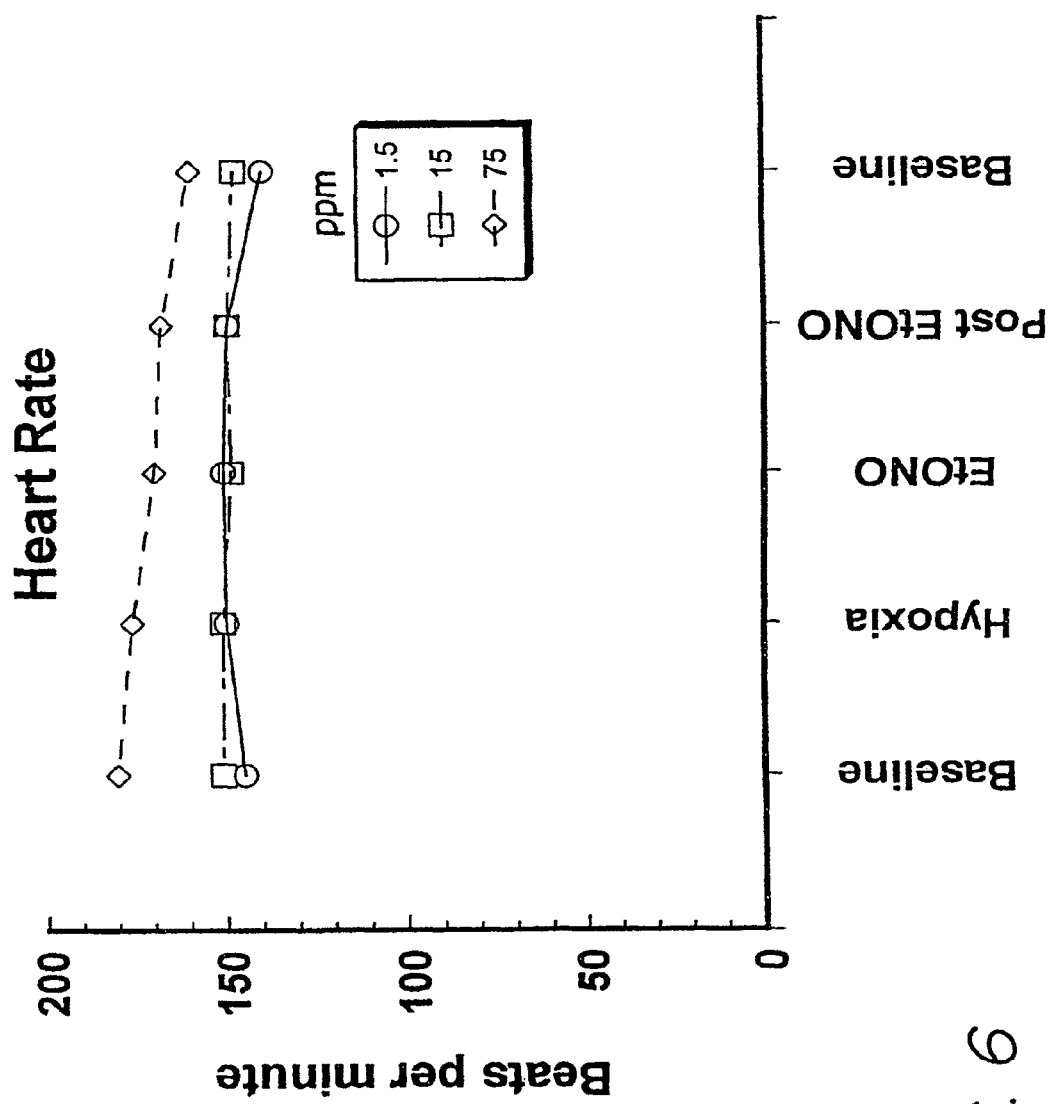
FIG. 6 depicts graphs of heart rate for three doses of ethyl nitrite gas and shows results of Example I.

FIG. 6 depicts graphs of heart rate in beats per minute for three concentrations of EtONO administration with data points at the same stages as for FIG. 1. The data shows that EtONO administration has no effect on heart rate.

Blood samples-taken during inhalation of the highest dose of EtONO administered (75 ppm) show methemoglobin content ranging from 0.5 to 4.5% (n=5), i.e., well within the acceptable physiological range.

Figure 7:
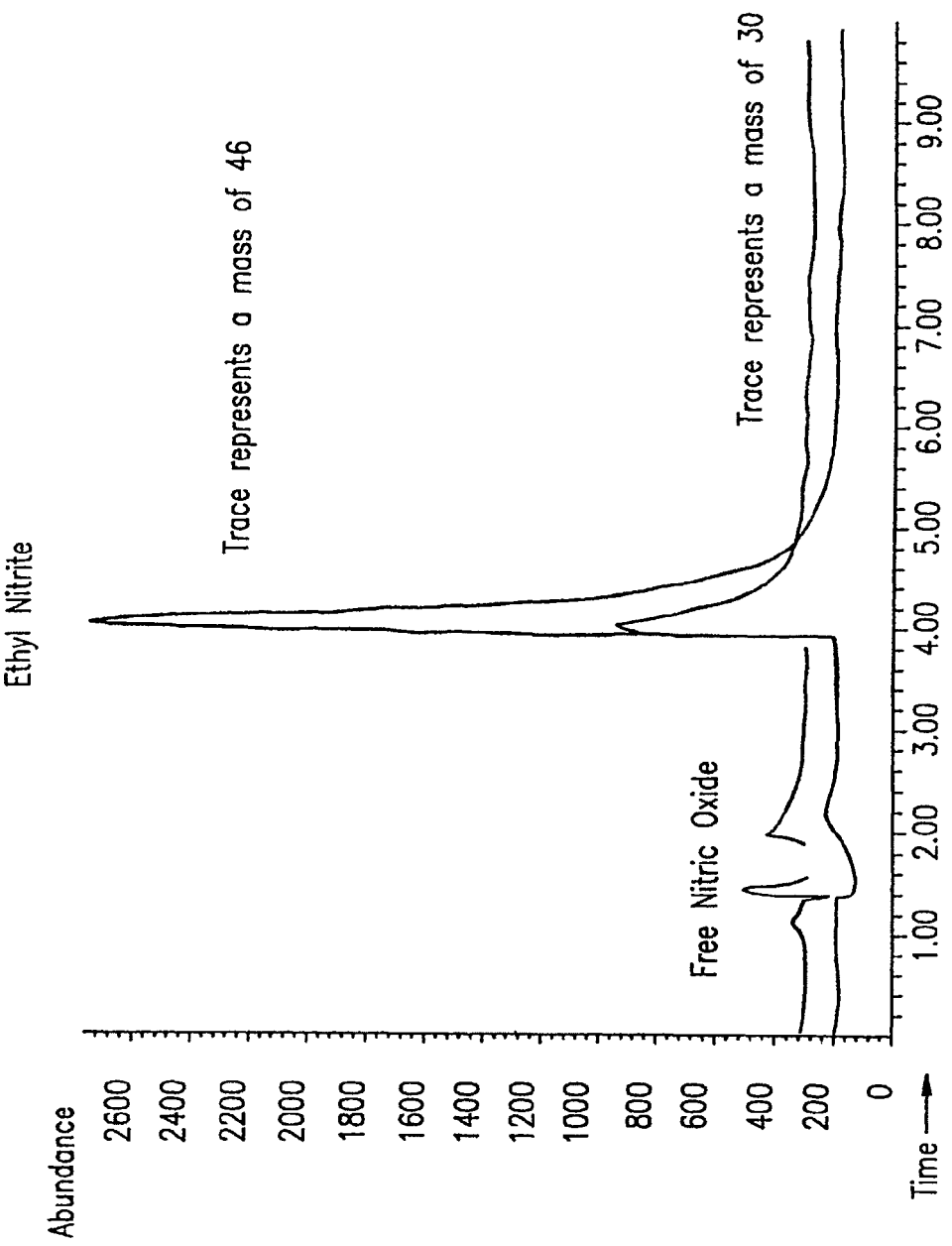
FIG. 7 shows gas chromatography/mass spectral analysis results on ethyl nitrite gas delivered through the ventilation system of Example I at 75 ppm.

Gas chromatography/mass spectrometer analysis on gas delivered on admixture of nitrogen ethyl nitrite admixture with ventilator output, at 75 ppm ethyl nitrite, was carried out. In particular, a 100 μl gas sample was taken from the expiratory arm of the respiration system (using a glove as a model lung) with ethyl nitrite being delivered from the system to the patient at 75 ppm. The gas sample was injected into an HP GC/MS system using a 30 m 0.53 μm GS-Q column. Ethyl nitrite is decomposed within the mass spectrometer producing ethanol (mass 46) and some NO (mass 30) but virtually no free NO was generated. The results are shown in FIG. 7. Unbound nitric oxide elutes from the GS-Q column at approximately 1.5 minutes and ethyl nitrite elutes from the column at 4.1 minutes. The data shows virtually no free NO or $NO_2$ is detected.

The experiment of this example was carried out to show reversal of pathologic symptoms an administration and was not to assess rebound. Rebound was not appropriately assessed because the subjects were still sufficiently hypoxemic at the conclusion of treatment, that the normal response of pulmonary artery pressure increase occurred as a result. Rebound is assessed in Example XII below.

In another case with piglets, increased $Pa_{O2}$ and decreased pulmonary vascular resistance was obtained with 100 ppm trifluoronitrosomethane in place of ethyl nitrite.

Example II

A 30-year-old white female with pulmonary pressures of 70/40 mm Hg is admitted into an intensive care unit and deteriorates due to right heart failure, and is given for inhalation through a face mask an admixture of $O_2$, $N_2$ and ethyl nitrite such that the $Pa_{O2}$ is maintained at 90 and ethyl nitrite is present at 70 ppm. Pulmonary pressures fall to 30/15 and right heart failure disappears.

In another case, an identical patient receives the same treatment except for 80 ppm inhaled NO in place of the 70 ppm ethyl nitrite. Pulmonary pressures drop but the patient develops airway hyperreactivity (slight wheezing) and a chemiluminescence analyzer shows threefold increase in $NO_2$ concentration in exhaled air. Moreover, methemoglobin content in the blood is measured at 10%. The patient is switched from NO to inhaled ethyl nitrite (70 ppm), and $NO_2$ and methemoglobin levels drop and recovery is maintained.

Example III

A 60-year-old male cancer patient develops radiographic changes consistent with ARDS, post-chemotherapy. The patient's $Pa_{O2}$, falls to 50 mm Hg despite being on 100% oxygen and a right heart catheterization reveals a normal left ventricular endiastolic pressure. The patient is administered 40 ppm inhaled ethyl nitrite. The $Pa_{O2}$ increases to 70 mm Hg.

An identical patient is given 30 ppm inhaled NO and acute $Pa_{O2}$ improvement occurs but then clinical deterioration occurs characterized by worsening chest X-rays (due to inflammation) and renal impairment and $Pa_{O2}$ drops from 70 to 60 mm Hg. The patent is switched to 50 ppm inhaled ethyl nitrite and the radiographic changes and renal impairment stabilize and $Pa_{O2}$ increases to 90 mm Hg.

Example IV

A 26-year-old white female asthmatic gets intubated because of a severe asthmatic exacerbation. The patient is administered nebulized epinephrine and Atrovent but is failing to ventilate. The physician adds 100 ppm inhaled ethyl nitrite via a rebreathing face mask to the treatment, and the patient's $Pa_{O2}$ improves from 60 to 80 and ventilation becomes easier as evidenced by lower airway pressures (lung compliance).

Example V

A 12-year-old girl with cystic fibrosis presents with pseudomonal infection leading to pulmonary exacerbation. The patient is given nebulized antibiotics but continues to spike fever and do poorly. Inhaled ethyl nitrite is given at 80 ppm in oxygen with resolution of the infection over four days.

Example VI

A 65-year-old white male is admitted to a hospital with unstable angina. The patient is given i.v. nitroglycerin, heparin and a beta blocker. However, the patient continues to experience intermittent chest pain at rest. The patient is given 20 ppm inhaled ethyl nitrite in oxygen. The chest pain resolves.

Example VII

A 70-year-old white male presents with myocardial infarction. The patient's hematocrit is 26. The patient is given two units of blood but goes into heart failure. The patient is started on 60 ppm inhaled ethyl nitrite in nitrogen, with resolution of the heart failure. The patient also receives the standard medical regimen of tissue plasminogen activator, a beta blocker and an ACE inhibitor.

Example VIII

An 80-year-old presents with stage 3 biventricular failure and pulmonary arterial pressures of 50/30. The patient is given Captopril, digoxin and lasix but still has a systemic pressure of 140/80 with increased vascular resistance. The patient receives 80 ppm inhaled ethyl nitrite gas in oxygen. The patient's pulmonary pressures drop to 20/10 and systemic arterial pressure drops to 100/80 with normal peripheral vascular resistance. Ethyl nitrite administration is stopped and the pressures remain low.

Example IX

A 40-year-old black male presents with malignant hypertension (blood pressure of 240/160). The patient receives Captopril and nitroprusside and blood pressure drops to 200/120. The patient receives 80 ppm inhaled ethyl nitrite in nitrogen over the next day with an intravenous bolus of 200 mg/kg N-cetylcysteine administered at 6 hours after ethyl nitrite therapy was started. Blood pressure drops to 170/95.

Example X

An 18-year-old black female with homozygous sickle cell disease presents in painful crisis with chest radiographic changes and hypoxemia. The patient complains of severe abdominal and chest pain and is somewhat disoriented. She receives two units of blood while being administered 80 ppm inhaled ethyl nitrite in oxygen. All symptoms and radiographic changes resolve.

Example XI

A 60-year-old white male with leukemia presents with disseminated intravascular coagulation. A digit becomes ischemic. The patient is started on 80 ppm inhaled ethyl nitrite in oxygen and is given 100 mg/kg infusion of N-acetylcysteine. Blood flow improves to the digit.

Example XII

For a model of lung injury for acute respiratory distress syndrome (ARDS), pulmonary hypertension was induced in intubated neonatal pigs breathing 100% oxygen by repeated saline lavage (to remove surfactant), until the $Pa_{O2}$ fell below 100 mm Hg and stayed there for 30 minutes. Either NO or ethyl nitrite (EtONO) was administered by 2 hours. The NO was administered at 20 ppm for 10 minutes followed by 5 ppm. The EtONO was administered at 20 ppm. Results presented here are for $Pa_{O2}$ (FIG. 8) and for cardiac output (FIG. 9). Initial measurements were made (Control), then measurements were made repeatedly in the course of EtONO and NO administration, denoted (EtONO) and (NO), and then hemodynamics were retested every 5 minutes for 20 minutes after abrupt dissemination of inhaled gases (Post EtONO) and (Post NO). EtONO and NO were administered in oxygen gas.

Figure 8:
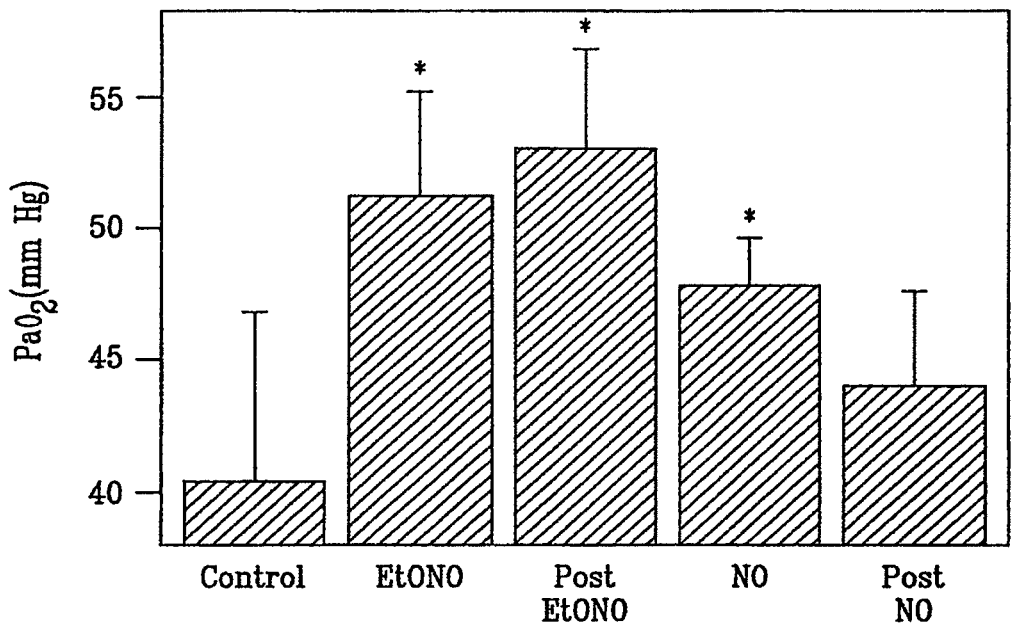
FIG. 8 depicts graphs of $PaO_2$ (i.e., $Pa_{O2}$) level without treatment, with treatment with ethyl nitrite (EtONO), post EtONO treatment, with treatment with NO, and post NO treatment and shows results of Example XII.
Figure 9:
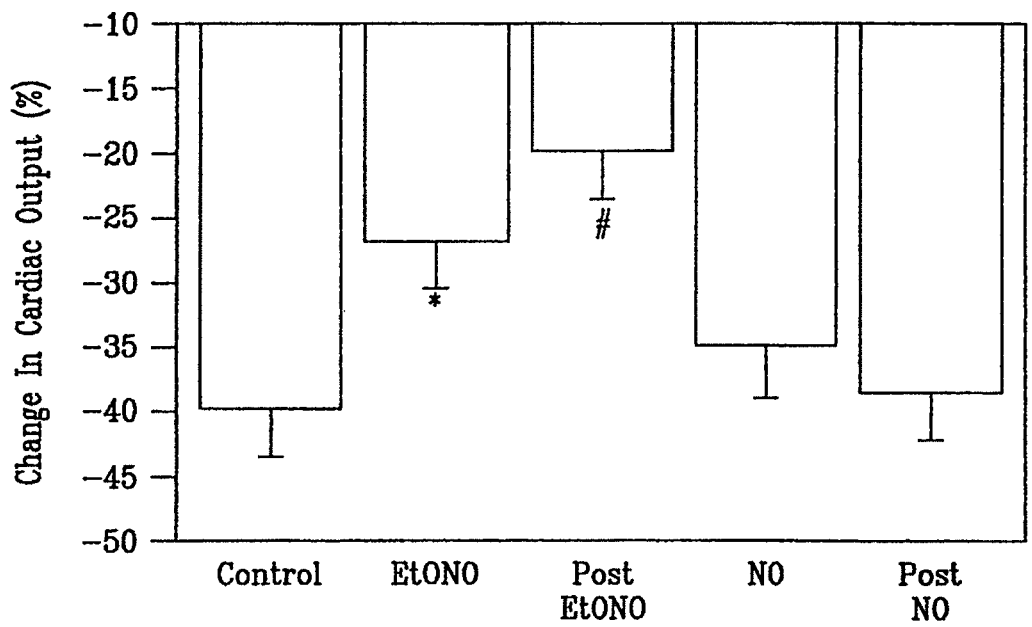
FIG. 9 depicts graphs of change in cardiac output without treatment, with treatment with ethyl nitrite (EtONO), post EtONO treatment, with treatment with NO, and post NO treatment and shows results of Example XII.

As shown in FIG. 8, EtONO administration caused significant increase in $Pa_{O2}$ at the two hour mark and post treatment there was further improvement. As shown in FIG. 8, NO administration caused significant increase in $Pa_{O2}$ at the 2 hour mark but post treatment there was rebound and lowering of $Pa_{O2}$. For EtONO, there was no change or better $Pa_{O2}$ levels for 20 minutes after administration was discontinued. For NO, there was a change for the worse 3 minutes after administration was discontinued. In addition, both drugs decreased pulmonary vascular resistance to comparable degrees but rebound occurred when NO was discontinued whereas pulmonary vascular resistance remained unchanged when EtONO was discontinued.

The results show that for EtONO administration, there is a dramatic improvement in blood oxygen levels at least as good as for NO during administration and no rebound and further improvement after discontinuance of treatment whereas with NO administration, there is rebound on discontinuance of treatment.

As shown in FIG. 9, EtONO administration caused increase in cardiac output from a level of minus 40% from normal (control animal had heart failure) to a significant increase in cardiac output to minus 27% from normal at the time of discontinuance of administration and further increase in cardiac output to about minus 20% from normal after discontinuance of treatment whereas NO administration did not cause significant increase in cardiac output.

The results depicted in FIGS. 8 and 9 were based on 15 pigs and in FIGS. 8 and 9, an asterisk represents significantly different from control (P<0.05).

The same scenario of increased $Pa_{O2}$ with no rebound and decreased pulmonary vascular resistance with no rebound and increased cardiac output with EtONO administration in contrast with increased $Pa_{O2}$ but with rebound and decreased pulmonary vascular resistance but with rebound with NO administration is observed in treatment of human adults for primary pulmonary hypertension or in the treatment of human babies with persistent pulmonary hypertension of multiple etiologies as exemplified in Example XIII below.

Example XIII

Ethyl nitrite has been used under the direction of one of the inventors herein to treat four human babies with persistent pulmonary hypertension and/or hypoxemia. The results were dramatic improvement in blood oxygen levels, no rebound, no methemoglobinemia and improvement in cardiac output. Pressor support was able to be stopped within a short period of time after EtONO therapy was started. One baby responded to ethyl nitrite that did not respond to NO.

Ethyl nitrite has been used to treat six adults with primary pulmonary hypertension. The results were improvement in blood oxygen levels, decrease in pulmonary vascular resistance and improvement in cardiac output.

There was no increase in methemoglobin.

Details on treatment of one baby with persistent pulmonary hypertension and one adult with primary pulmonary hypertension are set forth below.

A baby with persistent pulmonary hypertension administered epinephrine as required to maintain blood pressure, was administered 1.5 ppm ethyl nitrite (EtONO) for 15 minutes, then increasing to 75 ppm EtONO for the next 15 minutes, then 75 ppm EtONO for the next 30 minutes, then 15 ppm EtONO for the next 3 hours whereupon administration was stopped for 29 minutes and then NO was administered according to conventional treatment for 4 hours. The EtONO was administered via ventilator in the gas being administered via the ventilator. The initial $Pa_{O2}$ was 29 which is not compatible with life (and means the baby was dying). The $Pa_{O2}$ increased to 54 at the conclusion of EtONO therapy, then further increased to 86 during the about 30 minutes between treatments. Thus, there was improvement in the $Pa_{O2}$ with treatment with EtONO and no rebound after EtONO therapy was stopped. In contrast, the NO therapy caused a decrease in the $Pa_{O2}$ and at the end of 4 hours had to be stopped. The initial $PaCO_2$ (measure of how well lungs are ventilating) was 62 and reduced to 29 at the time of stopping EtONO therapy and as a result ventilation could be stopped. In addition, pressor support was able to be discontinued at the time of stopping of EtONO therapy.

We turn now to the case of treatment of an adult with primary pulmonary hypertension. The adult was given ethyl nitrite (EtONO) at 1.5 ppm for 10 minutes, 15 ppm for 10 minutes and 75 ppm for 10 minutes, and then EtONO therapy was stopped. As a result of the treatment, the mean pulmonary artery pressure dropped from 56 to 40, the cardiac output rose from 5.3 to 5.9 (which is good) and after treatment dropped to 5.6, the pulmonary vascular resistance reduced from 7.4 to 5.2 and the $Pa_{O2}$ increased from 79 to 94. The results show that the therapy worked to normalize hemodynamics. The goal was to improve oxygenation and lower pulmonary vascular resistance, and this was achieved.

Example XIV

This experiment was carried out to show that EtONO administration increases GSNO (nitrosoglutathione) in the lung, i.e., airway lining fluid, and that NO administration does not efficiently increase nitrosoglutathione concentration in the lung, thus predisposing to adverse reactions.

Figure 10:
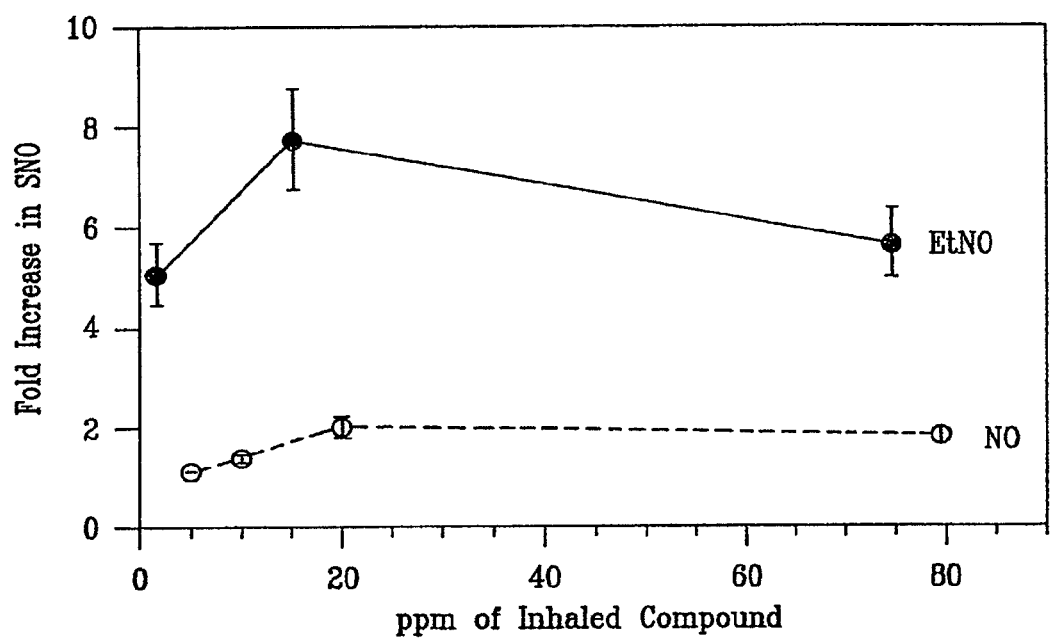
FIG. 10 is a graph of fold increase in airway SNO (nitrosoglutathione) with ppm of inhaled EtNO (ethyl nitrite) versus inhaled NO and shows results of Example XIV.

Ethyl nitrite (EtONO) or NO was added to the inhaled gas of neonatal pigs in doses as shown in FIG. 10. The EtONO was added at 0.6 liters/min into room air (20% oxygen). The NO was blended with 100% nitrogen. After 5 minutes, airway lining fluid in lung was sampled by bronchoscopy. Aspirates were colleted in phosphate buffered saline (PBS) containing 100 μM diethylenetriaminepentaacetic acid and assayed immediately for SNO content by chemical reduction-chemiluminescence, and for protein content by the Lowry method. SNO concentrations normalized to protein content are expressed as fold increase over endogenous levels (0.145±0.03 nM/μg for NO group, 0.22±0.04 nM/μg for EtONO group). Results are given in FIG. 10 where EtONO and NO doses expressed in ppm denote the X-axis and the Y-axis is fold increase in SNO. As shown in FIG. 10, EtONO at the lowest dose caused a 5-fold increase in GSNO and at all doses there is at least this increase. On the other hand, NO is shown to give a slight increase in SNO suggesting that most of the NO participates in an alternative chemical reaction with $O_2$ and/or reactive oxygen species which would be a basis for its toxicity. A conclusion is that EtONO loads natural glutathione to increase the pool of nitrosoglutathione (GSNO). FIG. 7 indicates that this occurs without the release of NO. Thus, EtONO administration selectively repletes lung SNO (i.e., increases SNO without causing the toxic effects that NO causes). Since depletion of GSNO occurs in patient's airway lining fluid with cystic fibrosis, asthma, hypoxemia and respiratory failure, treatment of these with EtONO is suggested. The data here suggests that a mechanism for the effect of EtONO is formation of GSNO whereas the mechanism for effect of NO is the relaxation effect of NO. Direct administration of GSNO into the lungs has to be carried out by nebulizing. As GSNO deposits in larger airways and does not cross cells, nebulizing it into the lungs does not cause it to distribute evenly. Moreover, patients cannot tolerate GSNO administration since it causes then to cough. Because of this, N-acetylcysteine administration has been tried; it does not work to increase GSNO levels. Thus direct administration of GSNO is not a substitute or alternative or equivalent for the invention herein.

Example XV

Figure 11A:
FIGS. 11A, 11B, 11C and 11D are graphs of tension versus time and show results of Example XV.
Figure 11B:
Figure 11C:
Figure 11D:

A volunteer patient with primary pulmonary hypotension and hypoxemia who has undergone right heart catheterization to assess responses to therapy, was treated with inhaled ethyl nitrite (EtONO) for 30 minutes with increasing dose titration from 1.5 to 75 ppm (1.5 ppm for 10 minutes, followed by 15 ppm for 10 minutes, followed by 75 ppm). The patient's red blood cells were drawn from an indwelling arterial line and measurements were carried out in rabbit aortic bioassays on intact red blood cells and on hemolysate obtained by lysing red blood cells with hypotonic saline. The rabbit aortic bioassays were carried out on rabbit aorta pieces hung on stirrups and attached to force transducers and measurement was carried out for increase and decrease in tension as described in Stamler, J., et al., PNAS, Vol. 89, 444-448 (1992). Assay was carried out at approximately 1% oxygen to simulate what would occur in tissues (which contain low $Pa_{O2}$). The results are shown in FIG. 11A (control for intact red blood cells, no treatment), 11B (intact red blood cells, EtONO treatment, 11C (control for hemolysate, no treatment), and 11D (hemolysate, EtONO treatment) which are tracings of tension (Y-axis) versus time (X-axis) with downward direction indicating relaxation and upward direction indicating contraction. As shown in FIG. 11A, one sees a small transient decrease induced by native red blood cells, but as shown in FIG. 11B, a significantly greater drop in tension induced by red blood cells from the EtONO treated patient. The reason for the ensuing increase in tension is that exporter in red blood cells releases all the activity. However, the activity is shown to be more than enough to achieve the biological effect desired. Turning now to the results on hemolysate, FIG. 11C shows hemolysate from native blood cells produces a very small relaxation under low $Pa_{O2}$ followed by a contraction whereas FIG. 11D shows hemolysate from blood cells from an EtONO treated patient produces a stronger dilation and no contraction compared to baseline. In FIGS. 11A, 11B, 11C and 11D, an asterisk represents significantly different from control ($p<0.05$) and # means p=0.06. The reason for the difference between the results for intact red blood cells and hemolysate is the hemolysate does not contain the functional exporter.

Measurements and data have indicated that in intact red blood cells and in hemolysate from EtONO treated patients, a mixture of nitrosylated hemoglobin and S-nitrosoglutathione is formed and that EtONO treatment increases the level of both (the nitrosylated hemoglobin and S-nitrosoglutathione being in equilibrium) in red blood cells in the patient.

Example XVI

Red blood cells are incubated with an alcohol solution of ethyl nitrite containing various concentrations of ethyl nitrite with a mole ratio of 1:50 ethyl nitrite to hemoglobin at 37° C. for 15 minutes. The result is red blood cells loaded with nitrosylated hemoglobin and nitrosylated glutathione in equilibrium and containing about 10 μM S-nitrosylated hemoglobin.

The resulting red blood cells are useful, for example, for treating sickle cell disease or ischemic disorder, e.g., angina.

Example XVII

Neonatal pigs as in Example XIV are administered inhaled gaseous drugs. After 5 minutes, airway lining fluid is sampled and assayed for nitrosoglutathione (GSNO) by the method described in Gaston, B., et al., PNAS, Vol. 90, 10957-10961 (1993). Screening shows that ethyl nitrite and amyl nitrite, but not NO, increase GSNO in airway lining fluid more than 50% compared to baseline.

Variations

Variations of the above will be obvious to those skilled in the art. Thus, the scope of the invention is defined by the claims.

What is claimed is:

1. A method for treating a patient by inhalation in need of improvement in tissue oxygenation or dilation of blood vessel or inhibition of clotting, comprising delivering into the lungs of said patient as a gas a therapeutically effective amount of a gaseous compound having an NO group that is bound in said compound so that the compound does not form $NO_2$ or $NO_x$ in the presence of oxygen or reactive oxygen species at body temperature, and wherein the compound is selected from the group consisting of ethyl nitrite, methyl nitrite, tert-butyl nitrite, trifluoronitrosomethane.

2. The method of claim 1, wherein the gaseous compound is ethyl nitrite.

* * * * *